United States Patent [19]

Doiron

[11] Patent Number: 5,533,508
[45] Date of Patent: Jul. 9, 1996

[54] VIVO DOSIMETER FOR PHOTODYNAMIC THERAPY

[75] Inventor: Daniel R. Doiron, Santa Ynez, Calif.

[73] Assignee: PDT Systems, Inc., Goleta, Calif.

[21] Appl. No.: 188,946

[22] Filed: Jan. 27, 1994

Related U.S. Application Data

[63] Continuation of Ser. No. 786,036, Oct. 31, 1991, abandoned.

[51] Int. Cl.$^6$ .................................................. A61B 5/00
[52] U.S. Cl. ..................... 128/634; 128/665; 250/484.2
[58] Field of Search ................ 128/633–4, 664–6; 250/484.1, 358.1, 458.1, 459.1, 327.25

[56] References Cited

U.S. PATENT DOCUMENTS

| | | | |
|---|---|---|---|
| 4,612,938 | 9/1986 | Dietrich et al. | 128/665 |
| 4,672,544 | 6/1987 | Chizallet | 250/370.07 X |
| 4,853,548 | 8/1989 | Stevens | 250/484.1 C |
| 4,859,853 | 8/1989 | Kronenberg | 250/370.07 |
| 4,880,986 | 11/1989 | Yamada et al. | 250/484.1 C |
| 4,957,481 | 9/1990 | Gatenby | 128/665 X |
| 4,976,266 | 12/1990 | Huffman et al. | 250/370.07 X |
| 4,981,138 | 1/1991 | Deckelbaum et al. | 128/665 |
| 4,998,930 | 3/1991 | Lundahl | 606/15 |
| 4,999,504 | 3/1991 | Braunlich et al. | 250/484.1 C |
| 5,015,855 | 5/1991 | Braunlich et al. | 250/484.1 C X |
| 5,028,794 | 7/1991 | Miller | 250/484.1 C |
| 5,030,834 | 7/1991 | Lindmayer et al. | 250/484.1 C |
| 5,041,734 | 8/1991 | Tetzlaff et al. | 250/484.1 C |
| 5,062,431 | 11/1991 | Potter | 128/665 |
| 5,079,429 | 1/1992 | Antonuk et al. | 250/370.09 |
| 5,091,653 | 2/1992 | Creager et al. | 250/484.1 C |
| 5,111,821 | 5/1992 | Potter | 128/665 X |
| 5,125,925 | 6/1992 | Lundahl | 606/15 |
| 5,275,160 | 1/1994 | Lilge et al. | 128/633 |

FOREIGN PATENT DOCUMENTS

| | | | |
|---|---|---|---|
| 0418588 | 3/1991 | European Pat. Off. | 250/484.1 C |
| 3110943 | 9/1982 | Germany | 250/484.1 C |

*Primary Examiner*—Angela D. Sykes
*Assistant Examiner*—Robert L. Nasser, Jr.
*Attorney, Agent, or Firm*—Michael G. Petit

[57] ABSTRACT

A device for measuring the fluorescence generated by photoactivated molecules during photodynamic therapy (PDT) and a method of using the device for dosimetry. The device, which comprises an isotropic spherical probe and detector electronics, simultaneously measures the space irradiance and time-integrated fluorescence during PDT. It is shown that there is a correlation between the time-integrated fluorescence generated during PDT treatment of a tumor and the delay in the regrowth of the tumor. The device provides the simultaneous measurement of the space irradiance and integrated fluorescence which measurements enable real time dosimetry during PDT.

2 Claims, 5 Drawing Sheets

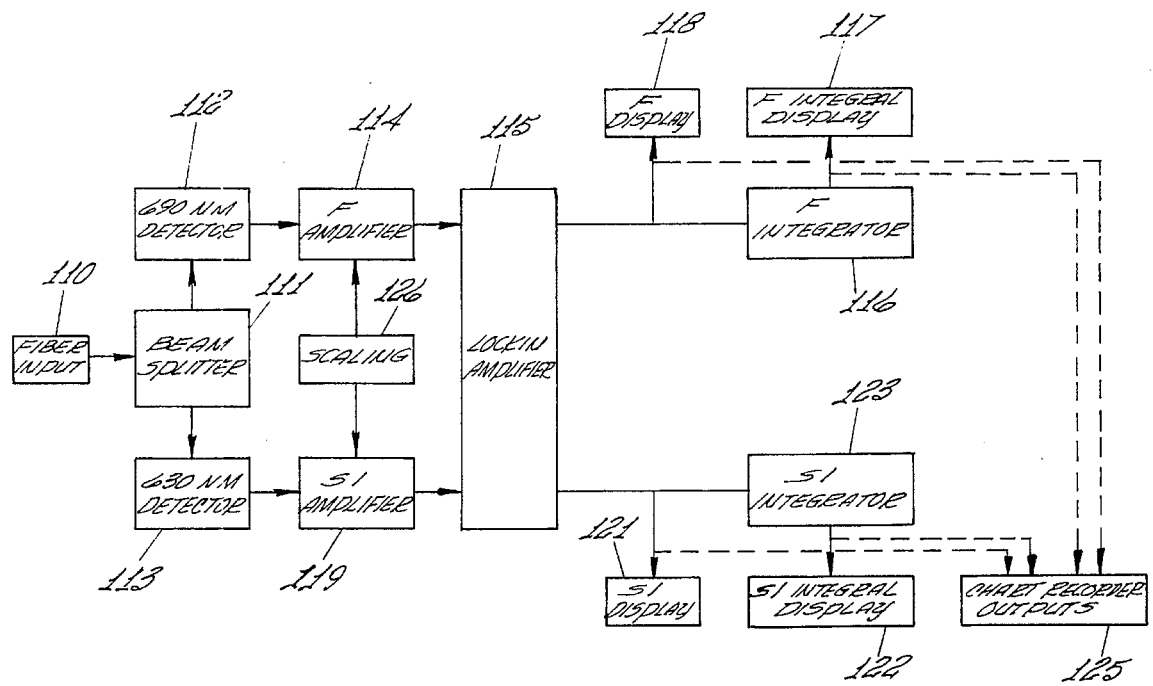
Fig 1 DOSIMETER BLOCK DIAGRAM
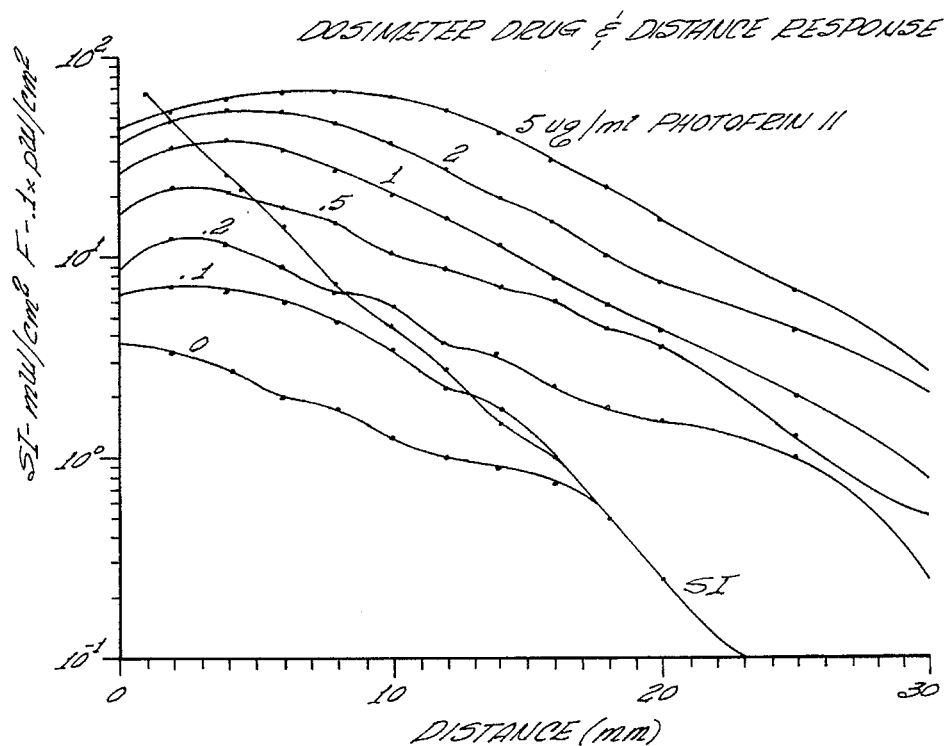
Fig 2 SI & F DISTRIBUTION IN TISSUE PHANTOM

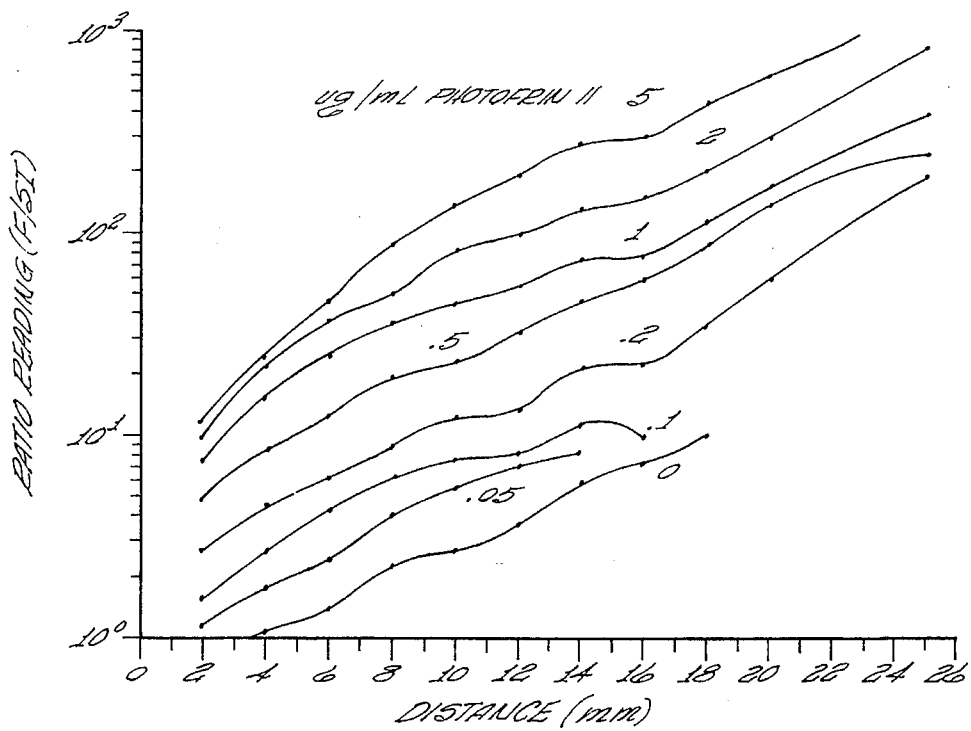
Fig 3a  F/SI RATIO DISTRIBUTION IN TISSUE PHANTOM
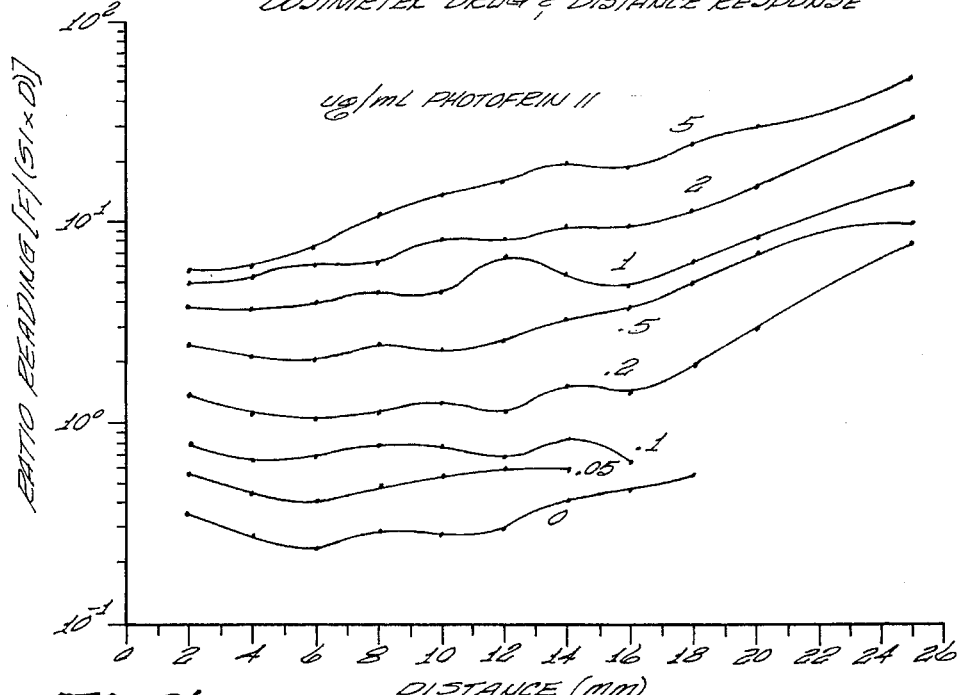
Fig 3b  INTRALIPID DIFFUSER W/ INK ABSORBER
F/SI × DISTANCE RATIO DISTRIBUTION IN TISSUE PHANTOM

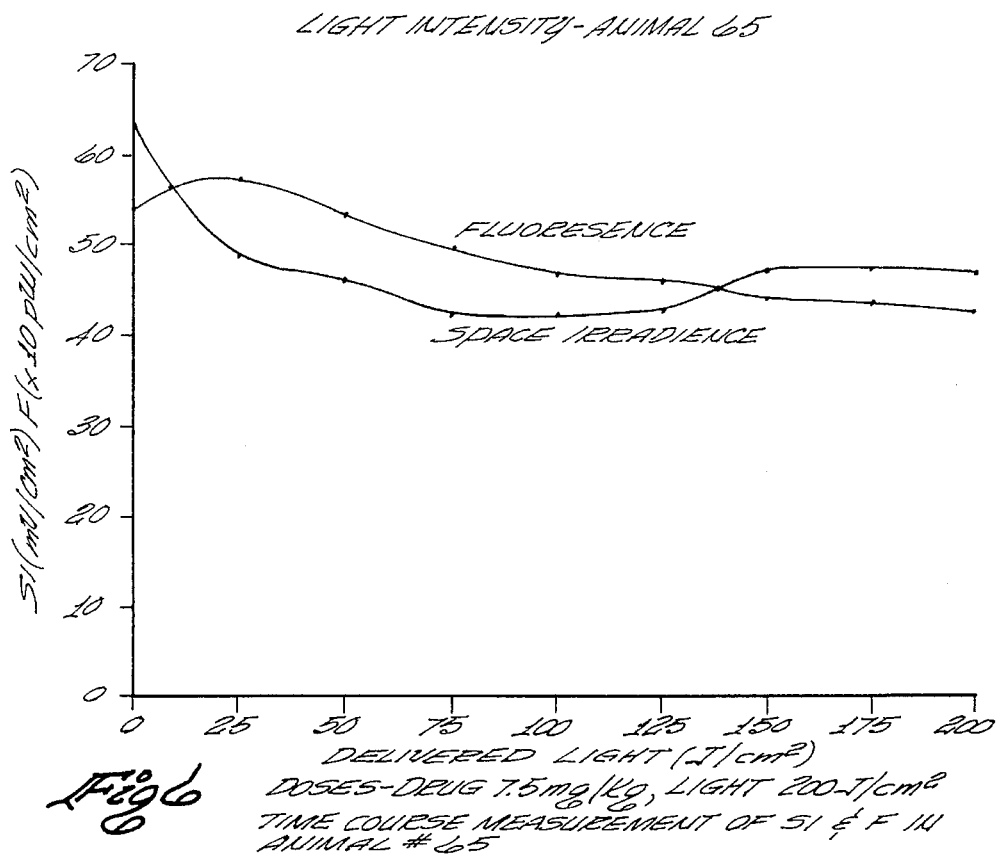
Fig 6 DOSES-DRUG 7.5mg/kg, LIGHT 200 J/cm²
TIME COURSE MEASUREMENT OF SI & F IN ANIMAL #65
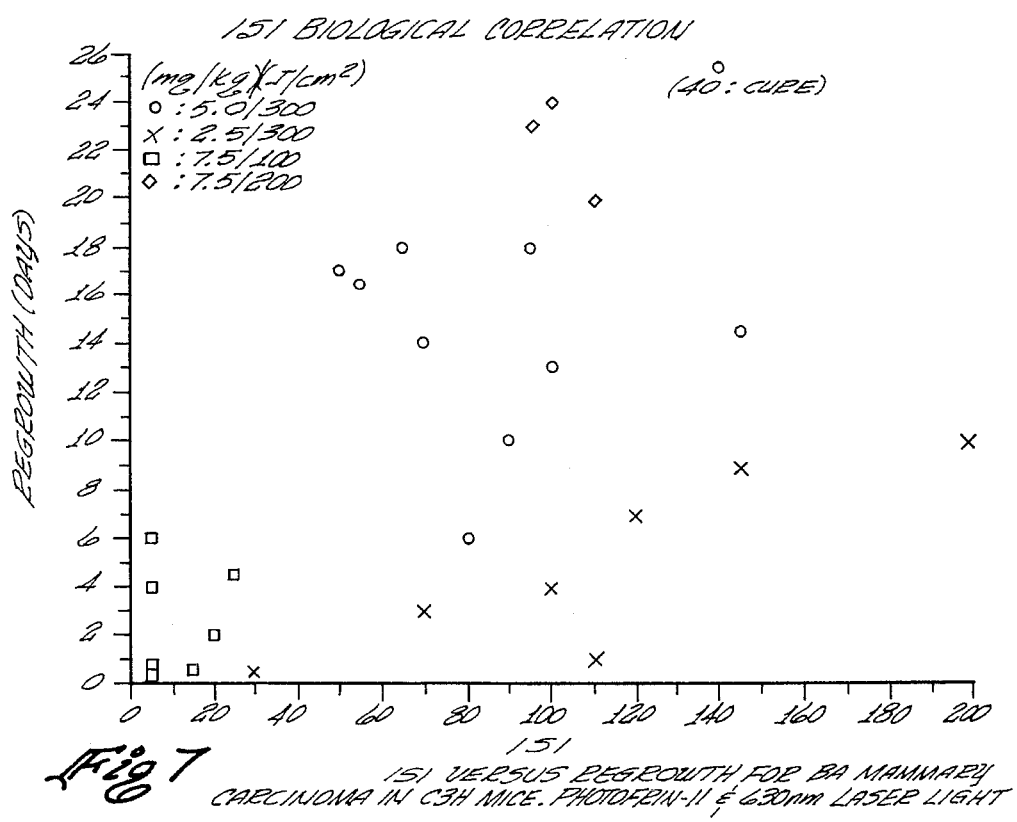
Fig 7 ISI VERSUS REGROWTH FOR BA MAMMARY CARCINOMA IN C3H MICE. PHOTOFRIN-II & 630nm LASER LIGHT

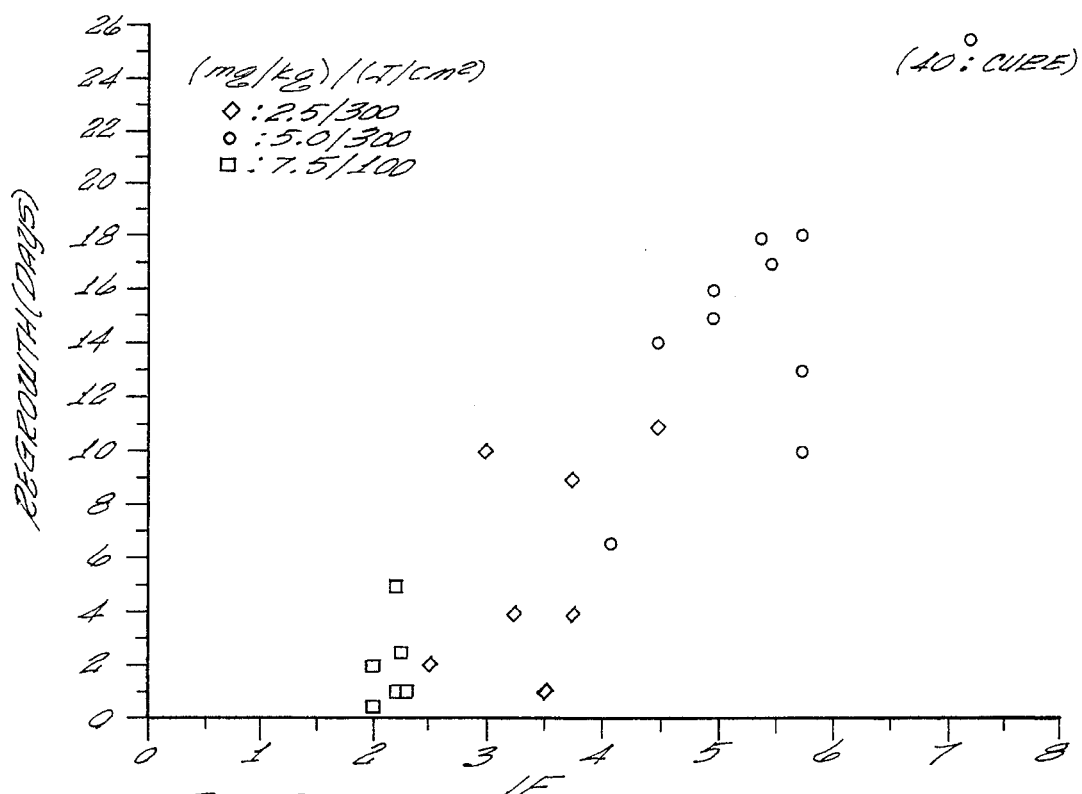

VIVO DOSIMETER FOR PHOTODYNAMIC THERAPY

CROSS REFERENCE TO RELATED APPLICATIONS

This is a continuation of application Ser. No. 07/786,036; filed Oct. 31, 1991, now abandoned.

BACKGROUND OF THE INVENTION

1. Field of the Invention

The present inventions relate to photodynamic therapy and more particularly to dosimetry in photodynamic therapy.

2. Description of the Prior Art

Photodynamic therapy (PDT) requires the selective activation of a biological response, either in vivo or in vitro, by the absorption of light by photosensitive compounds which are selectively taken up or retained by the biological target or its immediate environment. The response obtained by PDT depends on many different parameters. These numerous parameters and their interdependence makes it difficult to optimize the PDT process in an individual application or a specific target in a given application. Even with the present lack of ability to accurately control the various parameters, PDT has been shown to be highly effective in the treatment of a variety of diseases including cancer and viral infections.

PDT begins with the administration of a given amount of photosensitizer which is selectively taken up and/or retained by the biologic target (i.e. tissue, cells, or biologic target). After the photosensitizers are taken up by the PDT target, a light of the appropriate wavelength to be absorbed by the photosensitizer is delivered to the targeted area. This activating light excites the photosensitizers to a higher energy state. The extra energy of the excited photosensitizer can then be used to generate a response in the target area. This can be through the process of heating, chemical reaction or acoustical effects.

The net effectiveness of the PDT process will be dependent on the amount of photosensitizer at the target, the absorption properties of the environment around the target and photosensitizer, and a number of physiologic factors such as temperature, pH, oxygen content, and the sensitivity of the target to the photosensitizer generated reaction. The dependence of the response on so many factors makes the optimization of the PDT extremely difficult and requires the process to be extensively researched prior to its use and still cannot account for variables arising from one application to the next or from one patient to the next. What is truly required is a system that can monitor the photoactivation process in real time so that the PDT process can be controlled and optimized for each individual application.

Of primary importance in obtaining a satisfactory PDT response is concentrating sufficient photosensitizer in the target and delivering sufficient light to the photosensitizer. Once the photosensitizer absorbs the activating light, and is therefor excited, its path of de-excitation is independent of the wavelength of excitation. For a given photosensitizer the amount of excited photosensitizer that will de-excite by a given pathway depends on the structure of the compound and its binding in the surrounding environment. The probability that the excited photosensitizer will de-excite by a specific pathway is described by its quantum yield for that pathway. One of the methods of photosensitizer de-excitation is the emission of fluorescence or phosphorescence, (i.e. the emission of a photon of a longer wavelength, different color). Almost all of the photosensitizer molecules used in PDT have quantum yields for fluorescence that are finite and will emit some fluorescence photons. The number of these fluorescence photons will be directly proportional to the number of excited photosensitizer molecules and therefore directly proportional to the excited photosensitizer concentration in the target tissue and the intensity of the excitation light incident of the target tissue, or (space irradiance).

The number of fluorescence photons will also be influenced by factors that quench the photosensitization process in the same manner. This dependence of the fluorescence on the product of photosensitizer concentration and space irradiance is identical to that of the therapeutic photochemical reaction. For that reason the measurement of fluorescence generated during the PDT process should be directly proportional to the amount of photosensitization reaction generated.

SUMMARY OF THE INVENTION

With the present invention it is possible to measure the fluorescence generated during the PDT process and integrate it with time to get a quantitative number that is directly proportional to the total therapeutic PDT generated reaction. This number may be used to evaluate the progress of the treatment and to control the PDT process.

It is an object of the invention to provide a real time method for monitoring and controlling the PDT process, in vivo or in vitro, thereby making PDT a more accurate and useful clinical tool.

It is another object of this invention to provide a real time therapeutic dosimeter for PDT.

These and other objects of the invention will become apparent from a description of the preferred embodiment and viewing the illustrative drawings.

BRIEF DESCRIPTION OF THE DRAWINGS

FIG. 1 Schematic diagram of a system for the simultaneous measurement of space irradiance (SI) and fluorescence (F) of the photosensitizer.

FIG. 2 Shows the SI and F distribution in a tissue phantom

FIG. 3a Shows the F/SI ratio distribution in a tissue phantom

FIG. 3b Shows the F/SI×Distance distribution in a tissue phantom

FIG. 7 Shows the rate of tumor regrowth as a function of integrated space irradiance of photosensitizer molecules FIG. 8 Shows the rate of tumor regrowth as a function of the integrated fluorescence from photosensitizer molecules

DESCRIPTION OF THE PREFERRED EMBODIMENT

THE MONITORING SYSTEM

Figure 4:
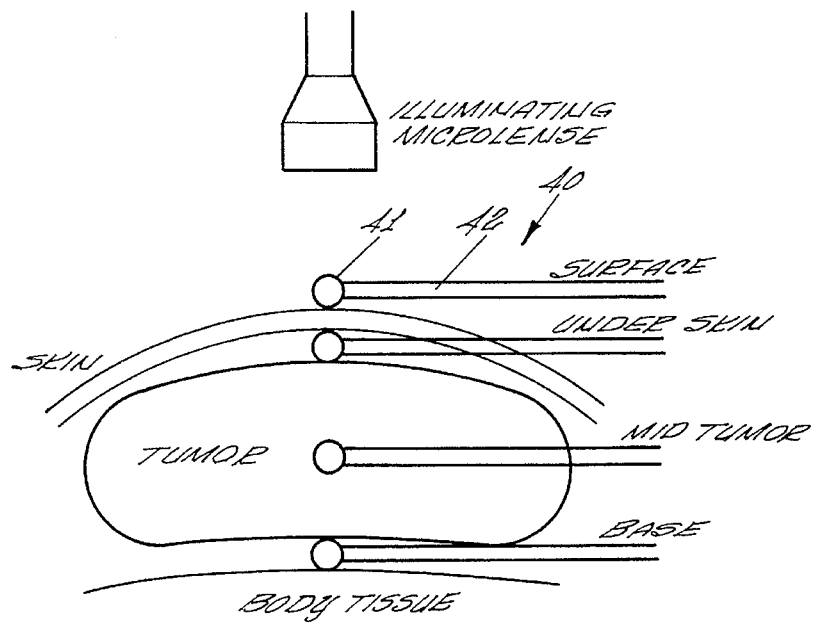
FIG. 4 Shows a longitudinal sectional view of an isotropic probe in various positions in and around a tumor under treatment FIG. 5 Shows the growth of a typical control tumor and the tumors treated with various drug and light combinations FIG. 6 Shows a typical measurement of SI and F in animal number 65

A monitoring system has been developed which, together with an isotropic probe, permits measurement of space irradiance, SI [nanowatts/sq-cm], and fluorescence, F [picowatts/sq-cm], of the photosensitizer, either separately or simultaneously. One such monitoring system suitable for the simultaneous measurement of SI and F is shown in FIG. 1. The light from the isotropic probe 110 enters a beam splitter 111 where a portion is directed to a fluorescence detector 112 tuned to the fluorescence emission band of the photosensitizer molecule. The fluorescence signal is amplified by an amplifier 114 and fed into a lock in amplifier 115. The remainder of the input light 110 exits the beam splitter 111 and is detected by an irradiance detector 113 tuned to the excitation wavelength. The irradiance detector 113 output is amplified 119 and fed into a separate channel of the lock-in amplifier 115. Since the irradiance signal 119 is so much larger than the fluorescence signal 114, the signal amplitudes must be adjusted by means of their respective amplifiers 119 and 114, and scaler 126 to approximately equal amplitudes before entering the phase comparator (not shown) in the lock-in amplifier. The fluorescence signal in phase with the chopped irradiating light exits the lock-in amplifier and is divided and fed to a fluorescence integrator 116 then to an integrated fluorescence display 117, and a fluorescence display 118. The fluorescence signal is processed by these components as is well known in the art and the amplitude recorded on a strip chart recorder 125. Similarly, the space irradiance light signal in phase with the chopping signal exits the lock-in amplifier 115 where it is divided and fed to a display 121, and an integrator 123, and a strip chart 125. The output of the integrator 123 can be either displayed 122 or recorded 125.

The system performs the time integration of both parameters as well as ratioing of F to SI. In order to measure the low level of fluorescence from the photosensitizer, PS, when activated with the red light typically used during PDT, (i.e. using Photofrin-II), the system utilizes lock-in amplifier technology. The F signal is at least a million times less than the SI for Photofrin-II. Using lock-in methods require the treatment light to be chopped with a duty cycle enabling rejection of the background and electrical noise. Unfortunately, chopping causes the loss of half of the treatment power and has significant impact on its practical clinical use, as will be discussed later.

Extensive bench and animal testing of the dual SI/F system shown in FIG. 1 has been performed. Its ultimate SI sensitivity is 1 microwatt/sq-cm but displays only down to 1 milliwatt/sq-cm since this is the practical level needed for PDT. The F sensitivity is 1.0 picowatt/sq-cm. A tissue phantom consisting of Photofrin-II in INTRALIPID® brand of a 10% soybean fat emulsion used for intravenous feeding (available from Kabivitrum Corp.) was employed to evaluate the system performance. The system has been found to be able to measure down to 0.1 ug/ml for photofrin-II in a tissue phantom with 630 nm activation, which is at least ten times less than believed to be present in tumors.

FIGS. 2 and 3a show the spatial measurements of SI, F and F/SI in the tissue phantom. As can be seen in the figures, it is possible to get a measured quantity directly related to the photosensitizer (PS) concentration without a depth correction. This is important in being able to measure quantitatively the PS concentration in tissue using the F signal to study PS uptake and retention. FIG. 3b shows the ratio of F/SI in FIG. 3a divided by the distance of the probe from the irradiating source. It is apparent from FIG. 3b that for small distances of the probe from the irradiating source, a measurement of F/SI×D can be used to determine the concentration of photofrin-II in the tissue. It could also be used as a possible measurement to predict a required therapeutic light dose. The very low level of the F signal when activated by the red wavelengths necessitated the use of lock-in amplifier techniques to accurately phase match the chopped treatment light to the detectors output signal to reject background noise. We were easily able to do this in the prototype systems and while doing the bench and phantom testing. When doing the biological testing though, it was found that continued and tight monitoring of the equipment during the long testing period (over six months) was required. Additionally, the loss of half the treatment power due to the chopping necessary to use lock-in techniques presents a practical problem. For these reasons we have investigated other possible electronic detection techniques to find a method more suitable for medical use.

More efficient quasi-CW pulsed lasers makes it possible to use other electronic detection methods giving the same sensitivity as lock-in amplifiers, but without the required phase matching and wasting of half the treatment light. Lasers in this category include the 532 nm doubled Nd:YAG pumped dye laser or the copper pumped dye lasers. Both of these lasers provide a quasi-CW output with high repetition rates (Khz) and long pulses (100 s of nanoseconds) to provide equivalent PS activation to CW argon pumped dye lasers. The efficiency of such lasers is at least ten times higher than the argon pumped dye laser rendering them suitable for medical use.

Accordingly, we are developing a digital-based detection system that can take advantage of the pulsed nature of these lasers to provide the needed sensitivity, reliability and ease of use to measure SI and F simultaneously. The new system (not shown) is based on the sampling of signals during the laser pulse and between the pulses. The latter allows for subtraction of the background, detector noise and ambient light similar to lock-in techniques but without the loss of activating light due to chopping. Averaging of numerous pulses, similar to box car average detectors, allows for improved accuracy and stability. This system will provide multichannel detection and measure SI and F and time integration of each. Since it is microprocessor-based, it can also provide time and spatial plotting and storage of the data.

THE ISOTROPIC PROBES

Three isotropic probes, compatible for use with the aforedescribed monitoring system, were developed for testing with animals as follows:

| | Isotropic Probes | |
| --- | --- | --- |
| Tip Size (mm) | Fiber Core Size (Microns) | Relative Sensitivity |
| 0.5 | 100 | 1.0 |
| 0.8 | 200 | 13.2 |
| 1.8 | 400 | 52.9 |

Turning now to FIG. 4, a tumor under treatment is shown in cross-section showing the isotropic probe 40 in a variety of positions. The isotropic probe, generally indicated at 40, comprises an isotropic head portion 41 and a pick-up fiber 42. The isotropic head portion 41, which is impregnated with light scattering particles (not shown), gathers light, both irradiating light from the illuminating source and fluorescence from the surrounding tissue, and conducts it to the detector (FIG. 1) by means of the pick-up fiber 42. The isotropic head 41 contains light scattering centers such as alumina in an optically transparent matrix and is preferably spherical to remove the directional sensitivity of the optical fiber. The outer diameter of the spherical isotropic tip is set to be twice the outer diameter of the pick-up fiber to minimize self-shielding of the response back along the fiber axis. With this ratio of tip-to-fiber outer diameters, the shielding due to the pick-up fiber represents less than a 1% correction from true isotropic response. The large increase in the difference in the relative sensitivity in going from the 0.5 mm to 0.8 mm is due to the increased fiber core size and the change in the fiber Numerical Aperture (NA). The scatterer concentration in the isotopic tip of each probe was optimized to provide an isotropic response while maximizing sensitivity.

EXAMPLE

Biological testing was conducted to determine if the SI, F or any combination of them could be used to predict the biological response in an animal tumor model system. For this work the C3H/HeJ mouse was used with the subcutaneous BA Mammary Carcinoma. Tumors were treated when 6 mm to 8 mm in diameter with varying Photofrin-II drug doses and 630 nm light doses, 24 hours post injection. The treatment method was surface illumination using 75 mw/sq-cm to assure no substantial hyperthermic conditions. The treatment matrix was:

|  | Light Dose (J/sq-cm) | | | |
| --- | --- | --- | --- | --- |
|  | 0.0 | 100 | 200 | 300 |
| Drug Dose (mg/kg) | | | | |
| 0.0 | 6 | — | — | 2 |
| 2.5 | — | — | — | 8 |
| 5.0 | 6 | — | — | 30 |
| 7.5 | 8 | 15 | 2 | — |

The light and drug combinations were chosen to give a scale of response from no response to no visible tumor at 40 days post treatment.

The normal positive response used in this tumor is no tumor present at 40 days post treatment. Such a binary response measurement does not allow for a meaningful correlation study. For this reason the regrowth of the tumor was used for the correlation study. The regrowth was measured by the volume of the tumor using the formula:

$$Volume=(PI/6) \times W \times D \times H$$

where:

PI=3.142

W=width of tumor at thickest point

D=thickness of tumor in a direction perpendicular to W

H=thickness in a direction normal to W and D

Figure 5:
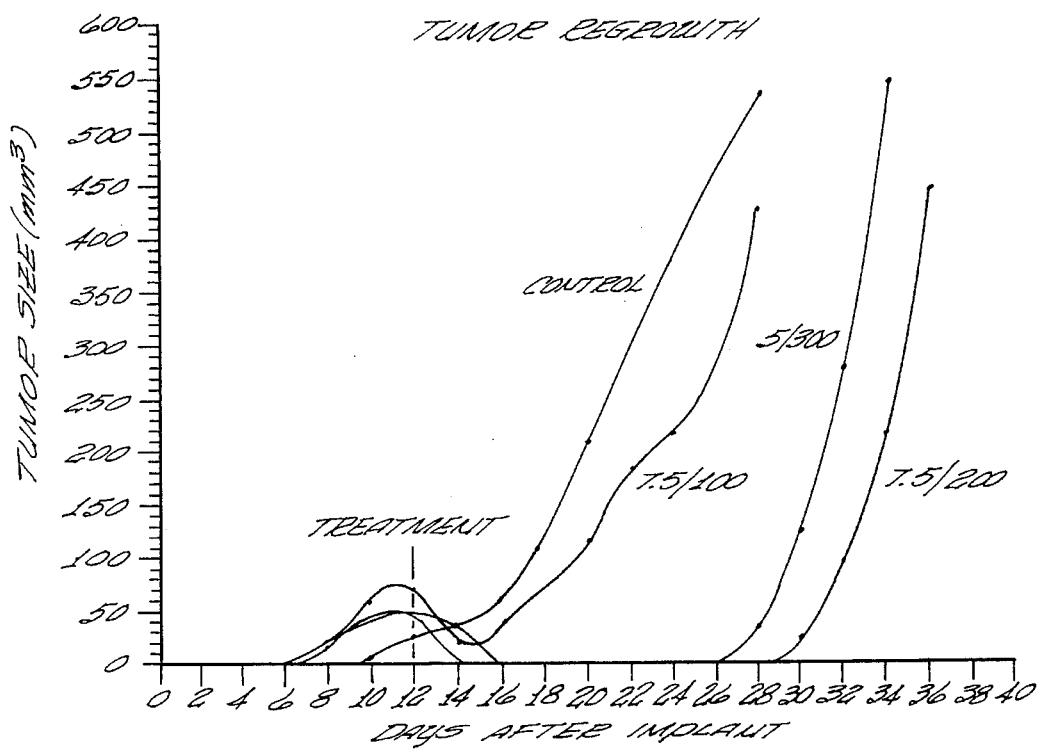

FIG. 5 shows the growth of a typical control tumor and the tumors treated with various drug and light combinations. Treatment is typically done at 12 days post implantation of the tumor. The treatment, typically, shows an initial drop in tumor volume with a delayed regrowth time that increases with the combination of drug and light dose. The end point used for the correlation study was the days for the tumor to regrow to its initial volume. For example, the 5 mg/kg and 300 J/sq-cm animal shown in FIG. 5 would have a delay period of 16 days.

The actual animal experiments included placement of the 0.8 mm isotropic probe at the base of the tumor, between the tumor and the muscle, using a positioning jig. The time course measurement of SI and F were recorded along with measurements taken on the surface of the tumor prior to and after treatment. FIG. 6 shows a typical time course measurement in animal number 65. Note the time variation of the signals during the treatment, even though the output of the dye laser is actively stabilized.

Control animals included: a) 12 animals treated without insertion of the probe, and b) 8 animals in which the probe was inserted, but no light. The latter group included animals with and without Photofrin-II. The insertion of the probe did not appear to disturb the growth of the tumor, which is expected since it is actually sitting underneath the tumor and on top of the muscle.

For experiments, the following was measured:

1. SI and F on top of the lesion pre and post light treatment (short exposure).
2. SI and F at the base of the tumor during treatment.
3. ISI and IF at the base of the tumor.

For evaluation of the correlation, the time integrating of SI and F, ISI and IF, respectively, was plotted in relationship to the regrowth time. The correlations evaluated included:

Integrated SI (=ISI)

Integrated F (=IF)

Ratio of F to SI (=F/SI)

Though the actual number of animals is limited, the plot of the data provided significant insight to possible correlations that might be useful. FIGS. 7 and 8 show the results obtained for ISI and IF, respectively. The results in FIG. 8 are typical of those obtained for all the parameter combinations except IF. This data shows a great deal of scatter with each combination of drug and light possibly having a different curve fit.

What is desired is a parameter that gives a one curve fit that adjusts for the variation of injected drug, light dose and animal variations. The IF parameter is the only one giving such a curve. Note that in FIG. 8 there are 25 points shown when 53 animals were actually treated at these data points. The remaining animals were either controls or lost to the study for technical reasons related to the measurement system (see note above about phase matching) or animal issues. This result makes some logical sense since the F value measured takes into account the amount of PS activated and its integration should be proportional to the total number of reactive molecules formed; i.e. singlet oxygen. It is, however, surprising that it does correlate so well considering that no adjustments are made for tumor thickness or attenuation variations between tumors. Other factors such as ISI may also have to be considered when considering different tumor types.

What I claim is:

1. A method for determining when a therapeutic dosage of treatment light has been delivered to photosensitive molecules within a diseased target tissue during phototherapy of the diseased target tissue comprising the steps of:

a) presenting a light probe having a non-invasive proximal end and an invasive distal end and a light conducting optical waveguide therebetween, the light probe being operable to receive light from a light source external thereto and incident upon the invasive distal end thereof and conducting the light to the non-invasive proximal end thereof; then b) placing the invasive distal end of the light probe in optical communication with the diseased target tissue; and c) presenting a light detector apparatus having a light input port adapted to receive light from the non-invasive proximal end of the light probe;

d) using said light apparatus for:
   (i) separating light consisting of fluorescent light and space irradiance entering the light input port into fluorescent light and space irradiance; and
   (ii) detecting the separated fluorescent light and space irradiance; and
   (iii) measuring the fluorescent light; and
   (iv) measuring the space irradiance; and
   (v) dividing the measured fluorescent light by the measured space irradiance, the quotient being the ratio of fluorescent light to space irradiance; and
   (vi) integrating the ratio with respect to time; then
e) irradiating the diseased target tissue with treatment light having a wavelength which is absorbed by the photosensitive molecules, and wherein a space irradiance portion of the treatment light delivered to the diseased target tissue enters the distal invasive tip of the light probe and wherein the absorption of treatment light by the photosensitive molecules causes at least a portion of the photosensitive molecules to emit fluorescent light; then
f) continuing irradiation of the target tissue until the integrated fluorescence reaches a predetermined value.

2. A dosimetry apparatus for measuring the dosage of photodynamic therapy administered to a diseased target tissue therapeutic light is absorbed by photosensitive molecules within the target tissue, some of which will thereafter produce a therapeutic effect within the diseased target tissue, and some of which will emit fluorescent light, the apparatus comprising, in combination:

a) an isotropic probe adapted to receive a portion of the therapeutic light delivered to a diseased target tissue and a portion of the fluorescent light being emitted by the photosensitive molecules in the diseased target tissue, the diseased target tissue being outside of said isotropic probe;

b) means for detecting and measuring said portion of the fluorescent light received by said isotropic probe; and c) means for detecting and measuring said portion of the therapeutic light delivered to the diseased target tissue;

d) means for dividing said measured portion of the fluorescent light by said measured portion of the therapeutic light, the quotient being the ratio of the portion of fluorescent light entering said probe to the portion of therapeutic light entering said probe; and e) means for integrating said ratio with respect to time, the resultant integral being the integrated fluorescence; and f) means for displaying said integrated fluorescence, said integrated fluorescence being a measure of the dosage of photodynamic therapy administered to the photosensitive molecule-containing diseased target tissue.

* * * * *

UNITED STATES PATENT AND TRADEMARK OFFICE
CERTIFICATE OF CORRECTION

PATENT NO. : 5,533,508
DATED : July 9, 1996
INVENTOR(S) : Daniel R. Doiron

It is certified that error appears in the above-indentified patent and that said Letters Patent is hereby corrected as shown below:

Title page, item [54] and col. 1, line 1, should read:

--IN VIVO DOSIMETER FOR PHOTODYNAMIC THERAPY--

Signed and Sealed this

Seventeenth Day of September, 1996

Attest:

BRUCE LEHMAN

*Attesting Officer*     *Commissioner of Patents and Trademarks*